United States Patent [19]

Pontigny

[11] 3,933,379

[45] Jan. 20, 1976

[54] SEPARABLE COUPLING BETWEEN TWO TUBES AND ITS PRODUCTION PROCESS

[76] Inventor: Jacques Pontigny, 14, Rue E. Legendre, 95 Margency, France

[22] Filed: Dec. 13, 1973

[21] Appl. No.: 426,724

[30] Foreign Application Priority Data
Dec. 22, 1972 France .............................. 72.46072

[52] U.S. Cl. .............................. 285/381; 285/137 R
[51] Int. Cl.² ........................................ F16L 47/00
[58] Field of Search ...... 264/230, 249, 25; 285/399, 285/381, 423, 374, 137 R

[56] References Cited
UNITED STATES PATENTS

| | | | |
|---|---|---|---|
| 1,677,221 | 7/1928 | Wertheimer .................... | 285/374 X |
| 3,382,121 | 5/1968 | Sherlock ......................... | 285/381 X |
| 3,453,007 | 7/1969 | Roland ............................ | 285/137 R |
| 3,634,924 | 1/1972 | Blake .............................. | 264/230 X |

FOREIGN PATENTS OR APPLICATIONS 903,757  8/1962  United Kingdom ................. 264/249

Primary Examiner—Werner H. Schroeder
Assistant Examiner—Peter Nerbun
Attorney, Agent, or Firm—Oldham & Oldham Co.

[57] ABSTRACT

The present invention concerns a separable coupling between two tubes.

According to the invention, a tube of a thermoplastic material which dilates under the action of heat and which retains its dilated form after cooling, is used as first tube, the extremity of the first tube is introduced in a sleeve of an elastomer material, which has an internal diameter at most equal to the external diameter of the second tube and which is inserted in a rigid hollow cylindrical body, provided at least at the end of the introduction of the first tube with an abutment for the sleeve, and the extremity of the first tube introduced in the sleeve is heated to dilate this extremity.

9 Claims, 2 Drawing Figures

SEPARABLE COUPLING BETWEEN TWO TUBES AND ITS PRODUCTION PROCESS

The present invention concerns a separable coupling between two tubes.

In the patent application for "Dilatable tube, method for its production and applications thereof" filed on the same day in the name of the same Applicant, a tube, which dilates under the action of heat, and retains its dilated form after cooling is described. This tube can be obtained by stretching a heated tube composed of a thermoplastic material irradiated with electron, and having an elastic memory activable above the ambient temperature, so as to reduce its diameter, followed by a cooling of the tube so stretched.

The Applicant has found that such a tube may be used to produce a coupling easily separable between two tubes.

According to the present invention, to produce such a coupling, a tube composed of a thermoplastic material which dilates under heat and retains its dilated form after cooling, is used as first tube, the extremity of this first tube is introduced into a sleeve of elastomer material, which has an internal diameter at most equal to the external diameter of the second tube and which is inserted in a hollow, rigid and cylindrical body of which at least the end in which the first tube is to be introduced, is provided with a stop ring for the sleeve, ring which leaves a free passage for the first tube, and the extremity of the first tube introduced in the sleeve is heated, so that this extremity dilates and thus compresses the sleeve and assumes a diameter greater than the sectional dimension of the free passage of the stop ring.

A hollow cylindrical body also provided at the other extremity with an abutment for the sleeve is advantageously used, so preventing any displacement of the sleeve of elastomer material.

As elastomer material, a material which well supports the heat, especially a silicone rubber, is advantageously used.

Other characteristics and advantages of the invention will appear from the description which follows and refers to the annexed drawing, in which.

Figure 1:
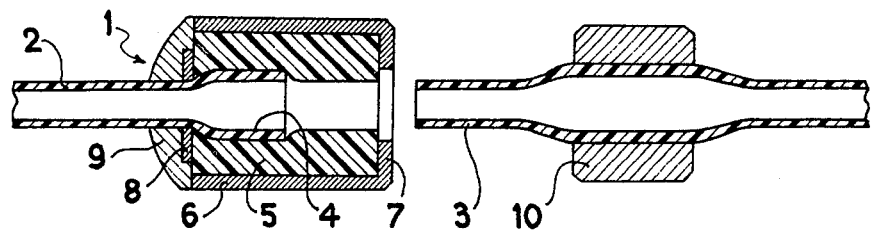
FIG. 1 is a cross section of a coupling according to the invention.

In FIG. 1, a coupling 1 is represented secured to a tube 2 in which a tube 3 can be introduced. The tube 2 is a polyethylene tube having an elastic memory (polyethylene irradiated with electrons) which has been stretched so as to reduce its diameter, this tube therefore being heat unstable in that it dilates under the effect of heat. The extremity 4 of this tube is inserted in the extremity of a silicone rubber sleeve 5. The sleeve itself is inserted in a rigid cylindrical tube 6 provided, at one of its extremities opposed to the end where the tube 2 is inserted, with an annular inwardly extending retaining portion 7 used as an abutment for the sleeve 5. A metal abutment 8 which is secured to the tube 6 by sticking with a thermosetting resin 9 and allows heating by induction, is also provided at the other end of the tube 6.

When the extremity 4 of the tube 1 is inserted in the sleeve 5, the abutment 8 is heated by induction so as to heat indirectly this extremity 4 to a temperature at least equal to the temperature which activates the elastic memory. This extremity 4 dilates and compresses the silicone rubber sleeve. This extremity thus becomes secured to the sleeve 5 and the tube 6.

The tube 3 shown in FIG. 1, which can be inserted in the sleeve 5, has a diameter slightly greater than that of the sleeve in order to assure by pressure a sealed junction. In the case shown in FIG. 1, the tube 3 is of the same nature as tube 2 and is provided with a metal ring 10 used as stop ring which has been secured to the tube 3 by heating this tube, for example in an indirect manner by heating the metal ring by induction.

Figure 2:
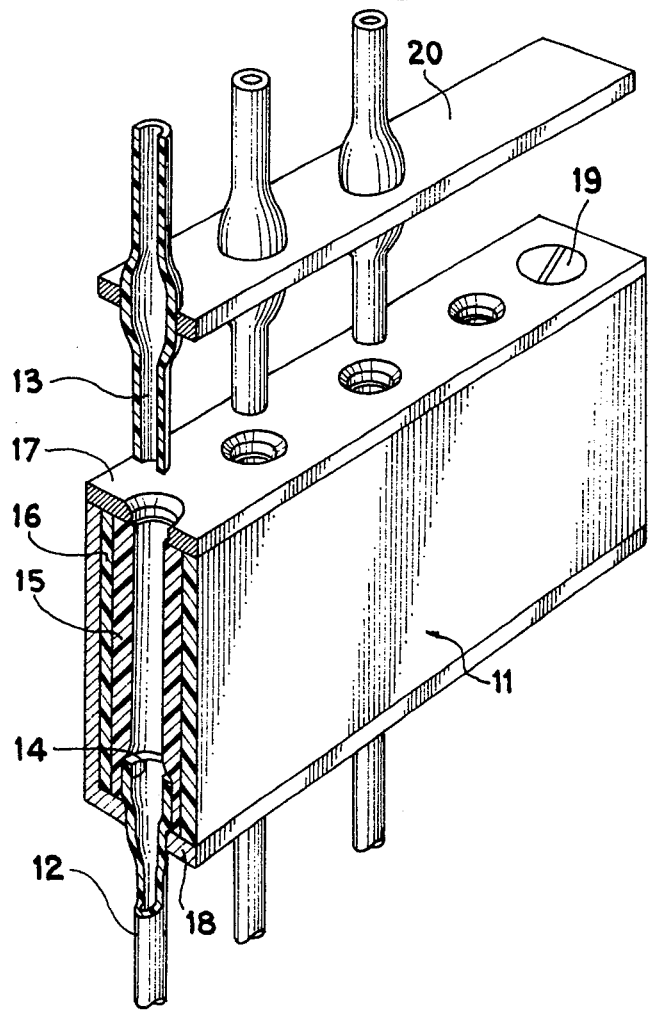
FIG. 2 is a view in perspective, with a partial section, of a device comprising several couplings according to the invention.

In FIG. 2 is shown a device containing several couplings of a type very similar to that shown in FIG. 1.

In a housing 11, several tubes, such as 12, similar to the tube 2 shown in FIG. 1 are assembled. The extremity 14 of these tubes is inserted in the sleeve, such as 15, of silicone rubber. These couplings are themselves inserted in parallel cylindrical holes provided in a rigid part 16. At each end of these cylindrical holes there are provided apertured plates 17 and 18 used as abutments for the sleeves 15.

These plates 17 and 18 are joined to the part 16 by a bolt and screw system 19. The plate 18, at the other side where the tube 12 are inserted, is a metal plate which can be used to heat indirectly the tube 12 by induction for example in order to obtain expansion of the extremity 14.

Tubes 13, which are of the same type as tube 3 in FIG. 1, fit into the sleeve. These tubes are secured to an apertured metal plate 20 by expansion under the effect of heat.

Such a system permits the simultaneous coupling of two series of tubes and may be used especially in automatic analysers.

While two complete embodiments of the invention have been disclosed herein, it will be appreciated that modification of these particular embodiments of the invention may be resorted to without departing from the scope of the invention.

Having now described my invention what I claim as new and desired to secure by Letters Patent is:

1. Process for the production of a separable coupling between a first tube and a second tube, comprising using a tube which is composed of a thermoplastic material having a plastic memory which dilates under the effect of heat and retains its dilated form after cooling as the first tube, introducing an end portion of the first tube into a first part of a bore of a sleeve of an elastomer material, the bore having a diameter at the most equal to the external diameter of the second tube, the sleeve being encompassed by means defining a hollow cylindrical body harder than the sleeve and having at an end of the body adjacent the first tube an abutment for longitudinally retaining the sleeve, which abutment has an edge defining a free passage for the first tube, heating said end portion of the first tube in the sleeve so that said end portion dilates and thus radially compresses the sleeve and assumes a diameter which is such that said dilated end portion extends radially outwardly beyond said edge of the abutment whereby the first tube is retained axially against movement in the body and sleeve in both directions, and inserting an end portion of the second tube in a second part of the bore axially adjacent said first part.

2. Process according to claim 1, in which the elastomer material is a silicone rubber.

3. Process according to claim 1, in which the abutment is of metal and is heated by induction so as to heat indirectly the end portion of the first tube.

4. Process for the production of a separable coupling between a first tube and a second tube, comprising using a tube which is composed of a thermoplastic material irradiated with electrons and having a plastic memory which dilates under the effect of heat and retains its dilated form after cooling as the first tube, introducing an end portion of the first tube into a first part of a bore of a sleeve of an elastomer material, the bore having a diameter at the most equal to the external diameter of the second tube, the sleeve being encompassed by means defining a hollow cylindrical body harder than the sleeve and having at an end of the body adjacent the first tube an abutment for longitudinally retaining the sleeve, which abutment has an edge defining a free passage for the first tube, heating said end portion of the first tube in the sleeve so that said end portion dilates and thus radially compresses the sleeve and assumes a diameter which is such that said dilated end portion extends radially outwardly beyond said edge of the abutment whereby the first tube is retained axially against movement in the body and sleeve in both directions, and inserting an end portion of the second tube in a second part of the bore axially adjacent said first part.

5. A coupling for separably coupling a first tube and a second tube, comprising a sleeve of elastomer material defining a throughway bore, means defining a hollow cylindrical body which encompasses the sleeve and is harder than the sleeve and has at a first end of the body an abutment for axially retaining the sleeve, the abutment having an edge defining a free passage for allowing the first tube entry into the bore of the sleeve before final assembly of the first tube with the sleeve and body, the bore of the sleeve having in the free state of the sleeve in the body and before introduction of the first and second tubes a diameter which is at the most equal to the diameter of the second tube, the first tube being of a thermoplastic material of a type having a plastic memory and capable of expanding upon application of heat and having an end portion which is engaged in a first part of the bore and is in an expanded state which is a result of application of heat to said end portion sufficient to activate said plastic memory, said expanded end portion having such diameter that it puts the sleeve in a radially compressed state in said first bore part and extends radially beyond said edge of the abutment whereby said end portion of the first tube is axially retained in the sleeve in both directions, the second tube being separably engaged in a second part of the bore axially adjacent said first part of the bore, and a metal stop ring engaging the second tube spaced from an end thereof, the second tube being of a thermoplastic material of a type having a plastic memory and capable of expanding upon application of heat and having an intermediate portion which is engaged with the metal stop ring and is in an expanded state which is a result of application of heat to said intermediate portion sufficient to activate said plastic memory, said expanded intermediate portion having such diameter that it puts the sleeve in a radially compressed state in said metal stop ring.

6. A coupling device for separably coupling a series of first tubes and a series of second tubes, the first tubes being composed of a thermoplastic material; comprising sleeve means of elastomer material defining throughway bores for respectively receiving the first tubes in a first part of the bores and the second tubes in a second part of the bores axially adjacent said first part of the bores, means defining a hollow body which at least partly surrounds the sleeve means to position them in parallel relation and is harder than the sleeve means and has at a first end of the body a transverse portion extending transversely of the bores of the sleeve means, the transverse portion defining a plurality of apertures which are coaxial with but of smaller size than the bores so as to constitute abutments for axially retaining the sleeve means, the apertures affording the corresponding first tubes a free passage so as to allow the first tubes to enter the corresponding bores before final assembly of the first tubes with the sleeve means and body, the bores of the sleeve means having in the free state of the sleeve means in the body and before introduction of the first tubes and second tubes a diameter which is at the most equal to the diameter of the corresponding second tubes the first tubes being of a type having a plastic memory and capable of expanding upon application of heat and having an end portion which is engaged in the first part of the corresponding bores and is in an expanded state which is a result of the application of heat to said end portion sufficient to activate said plastic memory, said expanded end portions of the first tubes having such diameter that they put the sleeve means in a radially compressed state in said first part of the bores and extend radially beyond the corresponding apertures whereby said end portions of the first tubes are axially retained in the sleeve means in both directions, the second tubes being separably engaged in the second part of the corresponding bores.

7. A device according to claim 6, further comprising, at an end of the body opposed to said first end and integral with the body, a plate defining a plurality of second apertures corresponding to and coaxial with the bores and allowing the passage of the second tubes, said plate retaining the sleeve means in the body.

8. A device according to claim 6, in which the second tubes are of a material of the same type as the first tubes and there is provided a second plate defining a plurality of second apertures, the second tubes extending through the respective second apertures and having a portion which is in an expanded state which is a result of the application of heat to said portion of the second tubes sufficient to activate said plastic memory, said expanded portions of the second tubes thus retaining the second tubes in the second apertures.

9. A coupling device for separably coupling a series of first tubes and a series of second tubes, comprising sleeve means of elastomer material defining throughway bores for respectively receiving the first tubes in one part of the bores and the second tubes in a second part of the bores axially adjacent said first part of the bores, means defining a hollow body which at least partly surrounds the sleeve means to position them in parallel relation and has at a first end of the body a transverse portion extending transversely of the bores of the sleeve means, the transverse portion defining a plurality of apertures which are coaxial with but of smaller size than the bores so as to constitute abutments for axially retaining the sleeve means, the apertures affording the corresponding first tubes a free passage so as to allow the first tubes to enter the corresponding bores before final assembly of the first tubes with the sleeve means and body, the bores of the sleeve means having in the free state of the sleeve means in the body and before introduction of the first tubes and second tubes a diameter which is at the most equal to the diameter of the corresponding second tube, the first tubes being composed of a thermoplastic material of a type irradiated with electrons and having a plastic memory and capable of expanding upon application of heat, the first tubes having an end portion which is engaged in the first part of the corresponding bores and is in an expanded state which is a result of the application of heat to said end portion sufficient to activate said plastic memory, said expanded end portions of the first tubes having such diameter that they put the sleeve means in a radially compressed state in said first part of the bores and extend radially beyond the corresponding apertures whereby said end portions of the first tubes are axially retained in the sleeve means in both directions, the second tubes being separably engaged in the second part of the corresponding bores.

* * * * *